United States Patent
Jayaraman et al.

(10) Patent No.: US 9,056,074 B2
(45) Date of Patent: *Jun. 16, 2015

(54) ORALLY BIOAVAILABLE STILBENOIDS—COMPOSITIONS AND THERAPEUTIC APPLICATIONS THEREOF

(75) Inventors: Krishnamani Jayaraman, Bangalore (IN); Muhammed Majeed, East Windsor, NJ (US); Jeffrey Reinhardt, Carson City, NV (US); Kalyanam Nagabhushanam, East Windsor, NJ (US); Samuel Manoharan Thomas, Bangalore (IN)

(73) Assignee: Sami Labs Limited, Bangalore (IN)

( * ) Notice: Subject to any disclaimer, the term of this patent is extended or adjusted under 35 U.S.C. 154(b) by 284 days.

This patent is subject to a terminal disclaimer.

(21) Appl. No.: 13/588,409

(22) Filed: Aug. 17, 2012

(65) Prior Publication Data
US 2013/0017605 A1 Jan. 17, 2013

Related U.S. Application Data

(60) Division of application No. 12/499,239, filed on Jul. 8, 2009, now abandoned, which is a continuation-in-part of application No. 12/367,840, filed on Feb. 9, 2009.

(51) Int. Cl.
| | |
|---|---|
| A61K 31/05 | (2006.01) |
| A61K 31/09 | (2006.01) |
| C07C 39/21 | (2006.01) |
| C07C 43/23 | (2006.01) |

(52) U.S. Cl.
CPC ............... *A61K 31/09* (2013.01); *A61K 31/05* (2013.01); *C07C 39/21* (2013.01); *C07C 43/23* (2013.01)

(58) Field of Classification Search
CPC ........ A61K 31/05; A61K 31/09; C07C 39/21; C07C 43/23
USPC .......................................... 514/733; 568/744
See application file for complete search history.

(56) References Cited

U.S. PATENT DOCUMENTS

2006/0205792 A1* 9/2006 Wong et al. .................... 514/352

OTHER PUBLICATIONS

Park et. al., Bioorganic and Medicinal Chemistry Letters, 2004, Elsevier, vol. 14, pp. 5895-5898.*

Ruan et. al., Chemistry and Biodiversity, 2006, Verlag Helvetica Chimica Acta, vol. 3, pp. 975-981.*

* cited by examiner

*Primary Examiner* — Sarah Pihonak

(57) ABSTRACT

A novel, bioavailable and safe stilbenoid 3,5-dimethoxy-3,4'-dihydroxystilbene represented by STR#1 with an unexpected enhanced ability to prevent the accumulation of lipids accompanying the terminal differentiation of adipocytes, thereby inhibiting adipogenesis, and nutraceutical and cosmeceutical compositions comprising 3,5-dimethoxy-3,4'-dihydroxystilbene useful for anti-obesity and anti-cellulite therapy, are disclosed. Further the enhanced SIRT-1 activation ability of 3,5-dimethoxy-3,4'-dihydroxystilbene represented by STR#1 and 2,3',5',6-tetrahydroxy-trans-stilbene represented by STR#II are disclosed. The enhancement of SIRT-1 polypeptide activity of the said compounds is unexpectedly much higher than resveratrol or its natural analog pterostilbene. Sirtuin modulating compositions comprising an orally bioavailable SIRT-1 enhancing compounds (i) 3,5-dimethoxy-3,4'-dihydroxystilbene represented by STR#I and (ii) 2,3',5',6-tetrahydroxy-trans-stilbene represented by STR#II are also disclosed. An additional embodiment, also discloses the enhanced anti-*Propionibacterium acnes* activity of 3,5-dimethoxy-3,4'-dihydroxystilbenes represented by STR#I and compositions thereof.

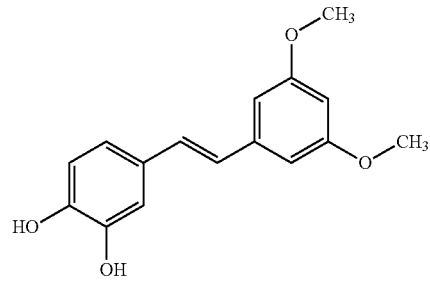

STR#I

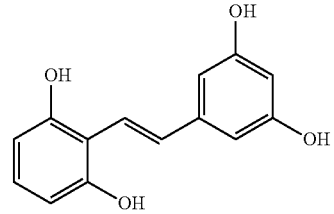

STR#II

1 Claim, 11 Drawing Sheets
(1 of 11 Drawing Sheet(s) Filed in Color)

Untreated 3T3-L1 mouse adipocytes

3T3-L1 mouse adipocytes treated with 3, 5-dimethoxy- 3, 4'-dihydroxystilbene

Adipocyte differentiation and fat accumulation

Inhibited Adipocyte differentiation and fat accumulation

ORALLY BIOAVAILABLE STILBENOIDS—COMPOSITIONS AND THERAPEUTIC APPLICATIONS THEREOF

This application is a divisional of U.S. patent application Ser. No. 12/499,239 filed on Jul. 8, 2009 now abandoned which is a continuation-in-part application of U.S. patent application Ser. No. 12/367,840 filed on Feb. 9, 2009.

BACKGROUND OF THE INVENTION

1. Field of the Invention

The present invention in general relates to natural fat modulators. More specifically, the present invention relates to novel, bioavailable and safe stilbenoid 3,5-dimethoxy-3,4'-dihydroxystilbene possessing an unexpected enhanced ability to prevent the accumulation of lipids accompanying the terminal differentiation of adipocytes, thereby inhibiting adipogenesis. Useful compositions thereof for anti-obesity and anti-cellulite therapy are also described in the invention. Further the present invention also discloses the enhanced SIRT-1 activation ability of 3,5-dimethoxy-3,4'-dihydroxystilbene and 2,3',5',6-tetrahydroxy-trans-stilbene. In addition, the present invention also discloses the enhanced anti-*Propionibacterium acnes* activity of 3,5-dimethoxy-3,4'-dihydroxystilbenes and compositions thereof.

2. Description of Prior Art

It is reported that dietary resveratrol (3,4',5-trihydroxy-trans-stilbene) at 50 parts per million suppressed blood serum lipid peroxidase levels in rats and dose-dependently suppressed serum triglyceride levels, VLDL and LDL cholesterol levels [Miura, D.; Miura, Y.; Yagasaki, K. Hypolipidemic action of dietary resveratrol, a phytoalexin in grapes and red wine, in hepatoma-bearing rats. Life Sci. 2003, 73, 1393-400]. Naokatu Arakaki et al reported that treatment of differentiated 3T3-L1 adipocytes with $H^+$-ATP synthase inhibitors (resveratrol; picceatannol) lead to a decrease in cytosolic lipid droplet accumulation.

Rimando et al.; document that pterostilbene (3,5-dimethoxy-4'-hydroxystilbene), a natural analog of resveratrol acts as a PPARα agonist and may be a more effective hypo-lipidemic agent than resveratrol itself [J. Agric. Food Chem. 2005, 53, 3403-3407]. This documentation is further validated by Marudhamuthu Amarnath Sateesh and Leelavinothan Pari, who observed that pterostilbene significantly, lowered levels of triglycerides, phospholipids, free fatty acids and total cholesterol in the serum, liver and kidneys of diabetic rats [Journal of Applied Biomedicine, Volume 5 (2008), No 1).

Similarly, Soon-he-Kim et al. reported (Biochemical and biophysical Research Communications 372 (2008) 108-113) that Vitisin A, a resveratrol tetramer inhibited adipocyte differentiation most effectively among others including resveratrol, stilbesterol, Ampelopsin A, Vitisin B, 3,4',5-Trimethoxy stilbene, and piceatannol. The study showed that 3,5-dihydroxy-4-methoxystilbene, 3,5-dihydroxy-4-methoxystilbene, 3,5-dihydroxy-4-methylstilbene acetate, resveratrol-3-O-B-D-glucoside, resveratrol-3-O-Glu hexaacetate, resveratrol triacetate, rhaponticin, rhaponticin hexaacetate, rhapontigenin, rhapontigenin triacetate, and e-viniferin had no effect on adipogenesis. This study is important prior art in that fat modulation through adipogenesis inhibition is not a common feature among all stilbenoids. Rather, there seems to be a phenomenon of selectivity operating in stilbenoids to inhibit adipogenesis based on their structure and substituted functional groups. While some stilbenoids better others in inhibiting adipogenesis, there are stilbenoids which totally fail to inhibit adipogenesis also.

Adding to the mounting body of evidence on the selective and variable effect of stilbenes towards fat metabolism/modulation, the present inventors disclose the adipogenesis inhibitory effect of 3,5-dimethoxy-3,4'-dihydroxystilbene. The present inventors have unexpectedly found that the adipogenesis inhibitory potential of the said molecule is 5000 times more effective than resveratrol, thereby finding use in anti-obesity and anti-cellulite therapy. The inventors have also found that the SIRT-1 modulatory effects of 3,5-dimethoxy-3,4'-dihydroxystilbene is far superior to resveratrol and pterostilbene enhancing its value as a nutraceutical agent. The molecule also shows considerable promise as a nutraceutical agent in terms of safety profile and bioavailability. In addition, the said molecule also shows far superior anti-acne activity in terms of its anti-*Propionibacterium acnes* activity when compared to resveratrol reported for the said activity. Also disclosed as a part of this invention is the enhanced SIRT-1 modulating compound 2,3',5',6-tetrahydroxy-trans-stilbene.

The principle objectives of the present invention include:

(a) To disclose a novel, orally bioavailable and safe stilbenoid with an unexpected enhanced ability to inhibit the accumulation of lipids accompanying the terminal differentiation of adipocytes, thereby inhibiting adipogenesis and compositions thereof suitable as cosmeceuticals, nutraceuticals and pharmaceuticals.

(b) To disclose a novel, orally bioavailable and safe enhanced sirtuin modulating stilbenoids and compositions thereof suitable as nutraceuticals and pharmaceuticals.

(c) To disclose novel stilbenoid inhibiting the growth of *Propionibacterium acnes* in an enhanced manner and compositions thereof suitable as cosmeceuticals.

The present invention fulfills the aforesaid principle objectives and provides further related advantages.

SUMMARY OF THE INVENTION

The present invention discloses

1. A novel, safe and bioavailable stilbenoid 3,5-dimethoxy-3,4'-dihydroxystilbene represented by STR#1 with an unexpected enhanced ability to prevent the accumulation of lipids accompanying the terminal differentiation of adipocytes, thereby inhibiting adipogenesis and cosmeceutical, pharmaceutical and nutraceutical compositions thereof useful for anti-cellulite and anti-obesity therapy.

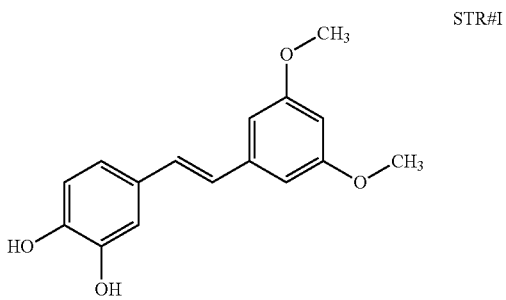 [SMILES: COc1cc(/C=C/c2ccc(O)c(O)c2)cc(OC)c1]

STR#1

2. A novel, safe and bioavailable stilbenoid 3,5-dimethoxy-3,4'-dihydroxystilbene represented by STR#1 with an unexpected enhanced ability for SIRT-1 polypeptide modulation (increased activity of SIRT-1 polypeptide) and cosmeceutical, pharmaceutical and nutraceutical compositions thereof.

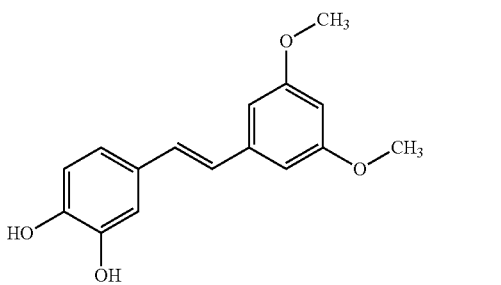

3. A novel, safe and bioavailable stilbenoid 3,5-dimethoxy-3,4'-dihydroxystilbene represented by STR#1 with an unexpected enhanced activity against *Propionibacterium acnes* and cosmeceutical compositions thereof.

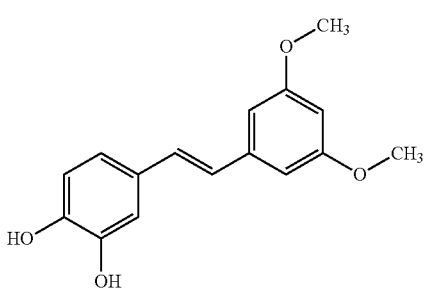

4. A novel, safe and bioavailable stilbenoid 2,3',5',6-tetrahydroxy-trans-stilbene represented by STR#II with an unexpected enhanced ability for SIRT-1 polypeptide modulation (increased activity of SIRT-1 polypeptide) and cosmeceutical, pharmaceutical and nutraceutical compositions thereof.

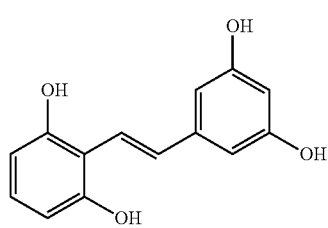

5. Adipogenesis inhibitors represented by the general structure STR#III, wherein $R_1=R_2$ are aliphatic or aromatic side chains and the resulting ether linkages thereof form primary, secondary or tertiary ethers.

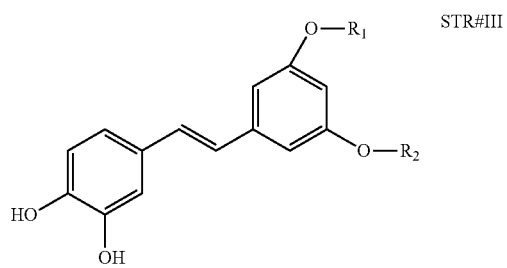

Other features and advantages of the present invention will become apparent from the following more detailed description, taken in conjunction with the accompanying drawings, which illustrate, by way of example, the principle of the invention.

BRIEF DESCRIPTION OF THE DRAWINGS

The patent or application file contains at least one drawing executed in color. Copies of this patent or patent application publication with color drawing (s) will be provided by the Office upon request and payment of the necessary fee.

DETAILED DESCRIPTION OF THE MOST PREFERRED EMBODIMENT (FIGS. 1, 1A, 1B, 2A, 2B, 3A, 3B, 3C, 4, 5A and 5B)

In the most preferred embodiment, the present invention discloses the novel, safe, bioavailable stilbenoid 3,5-dimethoxy-3,4'-dihydroxystilbene represented by SIR#1 with an unexpected enhanced ability to prevent the accumulation of lipids accompanying the terminal differentiation of adipocytes, thereby inhibiting adipogenesis and cosmeceutical, pharmaceutical and nutraceutical compositions thereof useful for anti-cellulite and anti-obesity therapy. 3,5-dimethoxy-3,4'-dihydroxystilbene is a natural stilbenoid occurring from plant sources including but not limited to *Pterocarpus marsupium* and *Vitis vinifera*. In a specific embodiment, the cosmeceutical compositions comprise from about 0.3% w/v to about 5% w/v of 3,5-dimethoxy-3,4'-dihydroxystilbene represented by STR#1. In yet another most preferred embodiment, the present invention includes adipogenesis inhibitors represented by the general structure STR#III, wherein $R_1=R_2$ are aliphatic or aromatic side chains and the resulting ether linkages thereof form primary, secondary or tertiary ethers. In one embodiment, the invention also encompasses pharmaceutical, cosmeceutical and nutraceutical compositions comprising the adipogenesis inhibitors represented by STR#III. In a specific embodiment, the cosmeceutical compositions comprise from about 0.3% w/v to about 5% w/v of the adipogenesis inhibitors represented by STR#III.

In yet another preferred embodiment, the present invention discloses the novel, safe and bioavailable stilbenoid 3,5-dimethoxy-3,4'-dihydroxystilbene represented by STR#1 with an unexpected enhanced ability for SIRT-1 polypeptide modulation (increased activity of SIRT-1 polypeptide) and pharmaceutical/nutraceutical compositions thereof.

In yet another preferred embodiment, the present invention discloses the novel, safe and bioavailable stilbenoid 2,3',5',6-tetrahydroxy-trans-stilbene represented by STR#2 with an unexpected enhanced ability for SIRT-1 polypeptide modulation (increased activity of SIRT-1 polypeptide) and pharmaceutical/nutraceutical compositions thereof.

As an additional embodiment, the present invention discloses the novel, safe and bioavailable stilbenoid 3,5-dimethoxy-3,4'-dihydroxystilbene represented by STR#1 with an unexpected enhanced activity against *Propionibacterium acnes* and cosmeceutical compositions thereof. In a specific embodiment, the cosmeceutical compositions comprise from about 0.3% w/v to about 5% w/v of 3,5-dimethoxy-3,4'-dihydroxystilbene represented by STR#1.

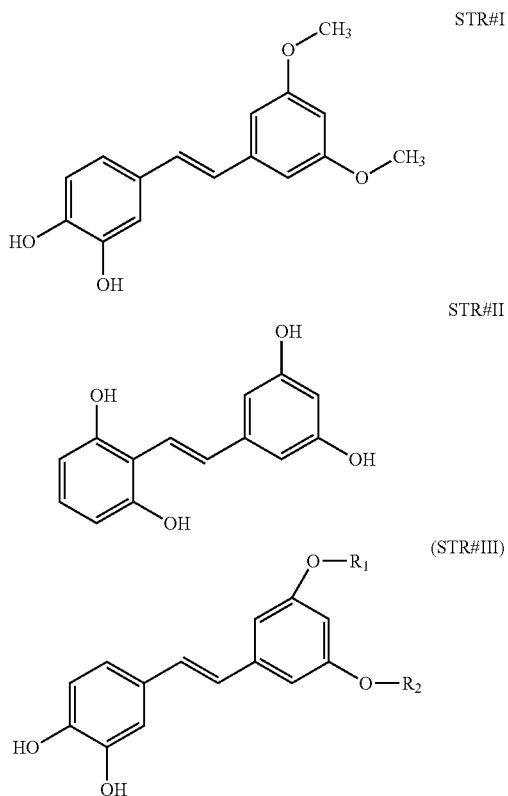

Figure 1:
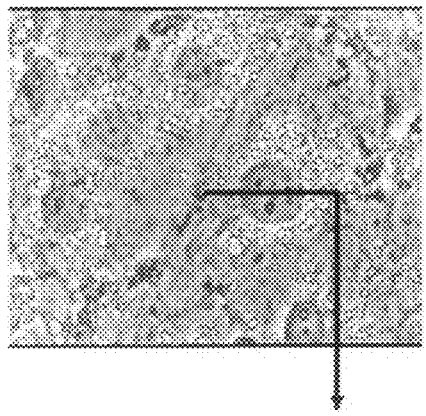
FIG. 1 represents the microphotographs showing inhibition of adipocyte differentiation and subsequent adipogenesis in 3T3-L1 mouse adipocyte cells which have been treated with 3-hydroxystilbene. The untreated cells show considerable lipid accumulation following adipocyte differentiation.
Figure 1:
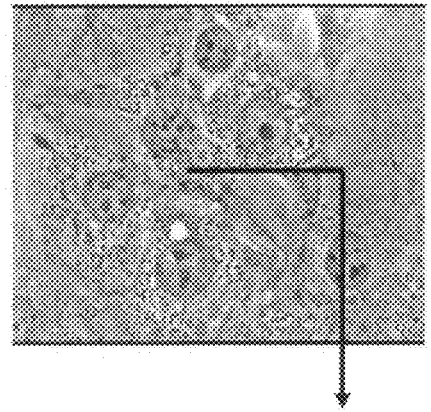

The underlying paragraphs discuss in detail as specific examples (i) Adipogenesis inhibition by 3,5-dimethoxy-3,4'-dihydroxystilbene (EXAMPLE 1; FIG. 1); (ii) the sirtuin modulating properties of 3,5-dimethoxy-3,4'-dihydroxystilbene and 2,3',5',6-tetrahydroxy-trans-stilbene (gnetol) in comparison (EXAMPLE 2, FIGS. 1A and 1B AND Table A) to resveratrol (3,4',5-trihydroxy-trans-stilbene), its natural methoxylated derivative 3,5-dimethoxy-4'-hydroxystilbene (pterostilbene) and Oxyresveratrol (trans-2,3',4,5'-tetrahydroxystilbene); (iii) Antimicrobial Studies of 3-hydroxy pterostilbene against *Propionibacterium acnes* (Example 3; TABLES B, C, D and E); (iv) Pharmacokinetics (EXAMPLE 4; FIGS. 2A, 2B, 3A, 3B, 3C, 4, 5A and 5B); (v) Formulations (EXAMPLE 5); (vi) Miscellaneous in-house data (EXAMPLE 6; TABLE F); (vii) Safety data

EXAMPLE 1

FIG. 1—Adipogenesis Inhibitory Activity

Principle:

A common assay to measure adipocyte differentiation in cell culture is with the dye Oil Red-O, which is a lipid-soluble red dye. Since terminal differentiation of adipocytes is accompanied by the accumulation of great amounts of lipids in large cytoplasmic vesicles, a strong, bright, staining of the cytoplasm with this dye is a reliable indicator of adipocyte differentiation.

Methodology:

3T3-L1 mouse adipocyte cells are seeded at a density of 5000 cell/200 μl of adipocyte induction medium in a 96 well plate. After 48 hrs varying concentrations of the sample are added. After 72 hrs, the medium is changed to adipocyte progression medium along with the sample. The medium is similarly changed after another 48 hours. The plates are washed gently after 48 hrs with 100 μl of PBS. 100 μl of 10% formalin is used to fix the cells for 30 min keeping at RT. The cells are then washed twice with 60% isopropanol gently. 100 μl of clear Oil red O stain is added to the wells & kept for staining for 1 hr. The cells are then washed with 70% Ethanol twice, once with PBS and air dried. Then 100 μl of 4% triton X-100 in isopropanol is added to all the wells covered tightly & kept it in a shaker for 20 min at 25-30° C. The OD reading is taken at 492 nm in microplate reader.

Calculation:

The results are expressed as $IC_{50}$ values using Graphpad prism software. The percentage of inhibition of adipogenesis is calculated as follows, $$\% \text{ Inhibition} = \frac{C-T}{C} \times 100$$

Where C-absorbance due to adipogenesis in untreated cells T-absorbance due to adipogenesis in sample treated cells.

Result:

(i) $IC_{50}$ of 3 Hydroxy Pterostilbene is 4.83 nM
(ii) $IC_{50}$ of Resveratrol is 25 μM
(iii) Reported $IC_{50}$ of pterostilbene is 23.9 μg/ml (Approximately 96 .mu.m). [Modulation of lipid accumulation in 3T3-L1 cells by selected polyphenols and MalusX domestics extracts in an in vitro adipogenesis model-Connie M. Remsberg Jaime A. Yanez[1,2], Karina Vega-Villa[1,2,3], Jody K. Takemoto1,2, Preston K. Andrews[3], Neal M. Davies[1]. 1 Pharmacology and Toxicology Graduate Program, 2 Department of Pharmaceutical Sciences, College of Pharmacy, 3 Department of Horticulture and Landscape Architecture, Washington State University, Pullman, Wash. 99164-6414, USA]

Note: $IC_{50}$ is the concentration required for 50% inhibition of adipogenesis. Lower $IC_{50}$ indicates better efficacy.

3-Hydroxypterostilbene showed superior adipogenesis inhibitory potential as compared to Resveratrol in maturing pre adipocytes. 3 Hydroxypterostilbene is about 5000 times more superior to Resveratrol for inhibition of Adipogenesis and hence a superior molecule for anti obesity applications.

EXAMPLE 2

Figure 1A:
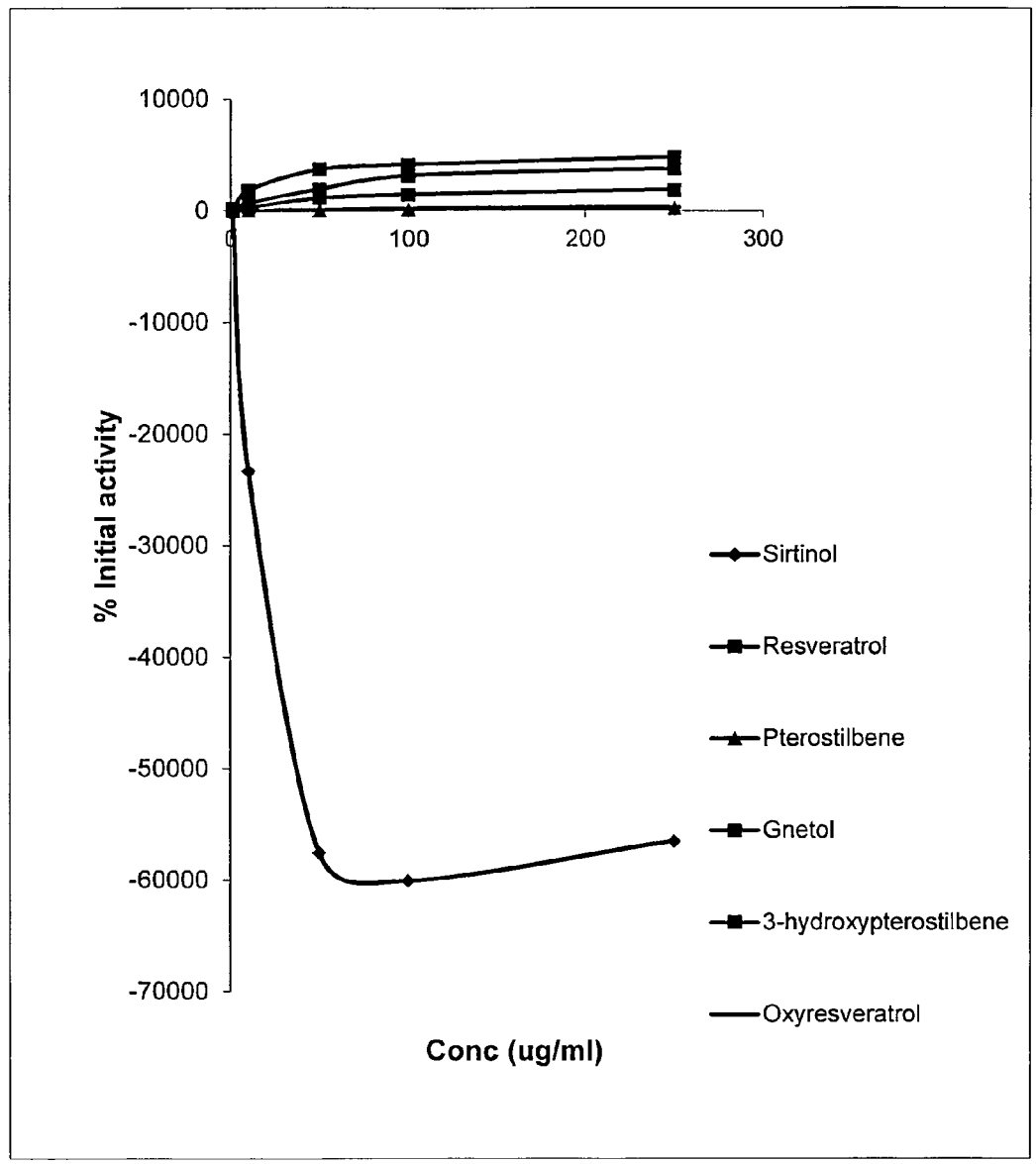
FIGS. 1A and 1B represents a graphical representation of the comparative percentage initial activity of the SIRT1 polypeptide activity with increasing concentrations of Sirtinol, Resveratrol, Pterostilbene, Gnetol, 3-hydroxypterostilbene (3 hp) and oxyresveratrol.
Figure 1B:
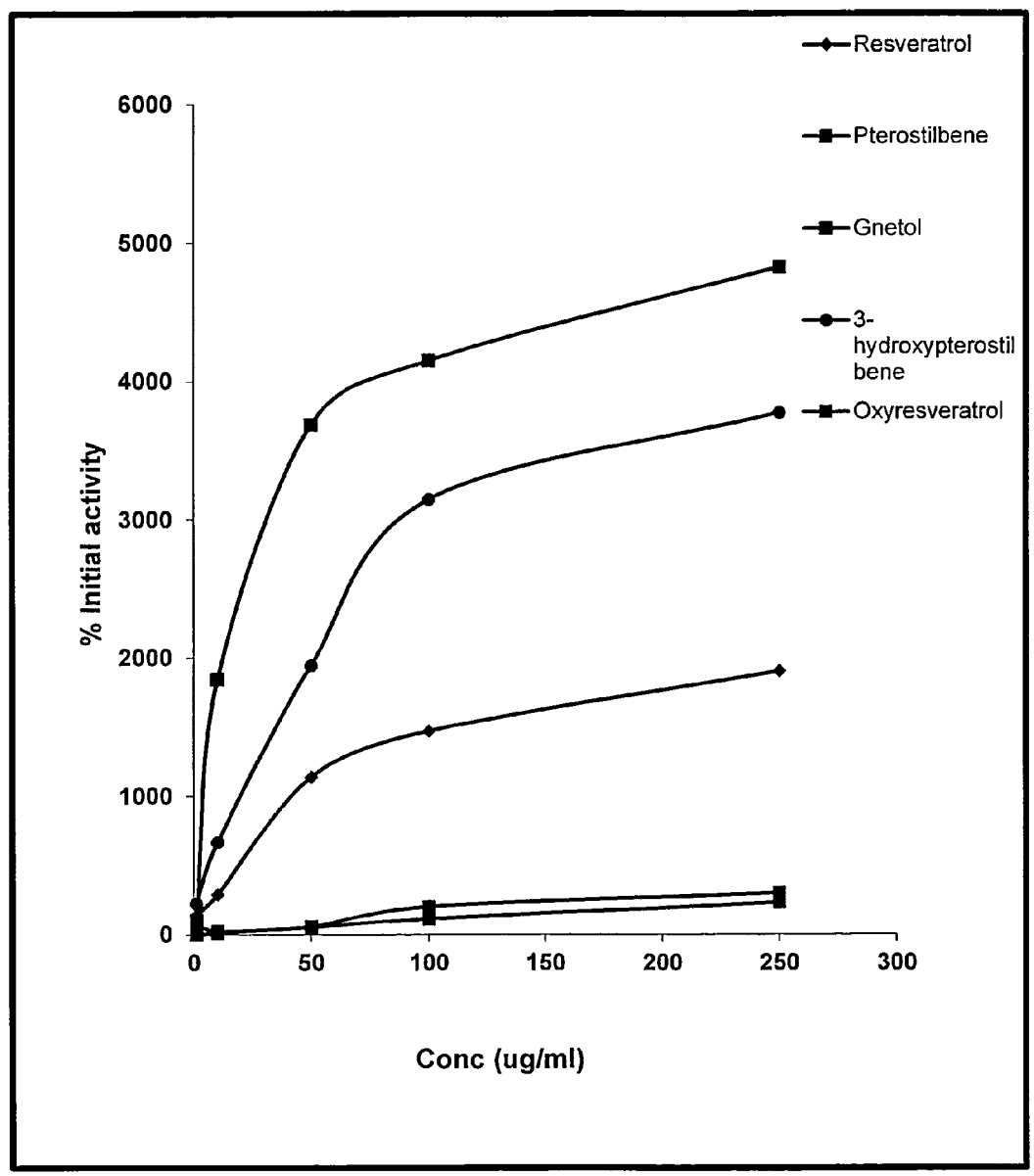

FIGS. 1A and 1B

SIRT-1 activation/inhibition was measured using the SIRT 1 Direct fluorescent Screening Assay kit (Catalog No.

10010401) and instructions provided therein of Cayman Chemical Company, 1180 East Ellsworth Road, Aim Arbor, Mich. 48108 USA.

TABLE A

Table A-Percentage SIRT 1 modulation by stilbenoids

| Concentration (µg/ml) | Sirtinol 2-[(2-Hydroxynaphthalen-1-ylmethylene)amino]-N-(1-phenyl-ethyl)•Benzamide | Resveratrol | Pterostilbene | Gnetol | 3-hydroxyPterostilbene (3hp) | Oxyresveratrol |
|---|---|---|---|---|---|---|
| 1 | 64.44 | 137.78 | 2.22 | 104.44 | 224.44 | 77.78 |
| 10 | −23326.67 | 291.11 | 11.11 | 1846.67 | 668.89 | 24.44 |
| 50 | −57517.78 | 1137.78 | 53.33 | 3686.67 | 1946.67 | 60.00 |
| 100 | −60093.33 | 1471.11 | 113.33 | 4151.11 | 3146.67 | 202.22 |
| 250 | −56544.44 | 1902.22 | 231.11 | 4826.67 | 3771.11 | 297.78 |

Results (Table A) and Discussion

It may be known from Table A that both 3,5-dimethoxy-3,4'-dihydroxystilbene (3-hydroxypterostilbene) and 2,3',5',6-tetrahydroxy-trans-stilbene (gnetol) show enhanced percentage SIRT 1 modulation in comparison to resveratrol, Pterostilbene and Oxyresveratrol at concentrations ranging from 10 µg/ml to 250 µg/ml. 2,3',5',6-tetrahydroxy-trans-stilbene (gnetol) proves to be a better SIRT 1 activator at concentrations ranging from 10 µg/ml to 250 µg/ml than 3-hydroxypterostilbene. Added advantage is the oral bioavailability of these two compounds, namely 3,5-dimethoxy-3,4'-dihydroxystilbene (3-hydroxypterostilbene 3 hp) and 2,3',5',6-tetrahydroxy-trans-stilbene (gnetol) as demonstrated by our data in FIG. 2A, FIG. 2B, FIG. 3A, FIG. 3B, FIG. 3C, FIG. 4, FIG. 5A & FIG. 5B.

EXAMPLE 3

Tables B, C, D and E

Antimicrobial Studies of 3-Hydroxy Pterostilbene Against *Propionibacterium acnes*

Objective: To compare the effect of 3-Hydroxypsterostilbene and Resveratrol on *Propionibacterium acnes* growth.

*Propionibacterium acnes* is a gram-positive, non-spore forming, anaerobic, pleomorphic rod found in clinical specimens. In human body *P. acnes* thrives on areas most exposed to air, such as the face and the nose. Its ability to live as an anaerobic in an air-exposed environment comes from the fact that *P. acnes* lives in the microhabitat sebaceous follicles thus causing acne vulgaris.

Method: Disc diffusion method was done to study Minimum inhibitory concentration (MIC).

Materials
1. *Propionibacterium acnes* ATCC 11827
2. Physiological saline or Buffered peptone water (BPW).
3. Reinforced clostridium medium (RCM) Hi-media
4. Reinforced clostridium agar (RCA) Hi-media
5. Anaerobic chamber.
6. Gassing manifold Nitrogen, mixed gases.
7. Spectrophotometer (600 nm to 625 nm).
8. Sterile Petri plates (150 mm×90 mm).
9. Sterile micro pipettes and sterile micro tips.
10. Sterile disc 6 mm.
11. Samples tested: Resveratrol (Batch No.: C81173) and 3-Hydroxypsterostilbene (Batch No.: P80096)

Methods

Anaerobic Chamber

The chamber used in the study is of COY LABORATORY USA model 8301-230, 3 ft polymer. The anaerobic chamber consists of a main chamber where in all the operations and incubation of the culture are carried out and a transfer chamber which is meant for taking the materials in and out of the equipment. The main chamber is provided with a heated fan box in order to maintain the required temperature (37° C.) and to circulate the air in the chamber. A catalyst stakpak is fixed to this fan box which consists of palladium catalyst, which is meant to convert oxygen to water molecules by reacting with hydrogen molecules. The anaerobic condition in the chamber for this is maintained by initialization with Nitrogen gas and then by the Mixture gas of $N_2+H_2+CO_2$ in the proportion 80:10:10. Two gas tank arrangements have been done where only $N_2$ is connected to the transfer chamber.

Preparation of the Inoculum *Propionibacterium acnes* ATCC: 11827

To carry out the antimicrobial activity of the products against *P. acnes* the organism was first cultured in the anaerobic conditions. Culture was inoculated into pre-sterile reinforced Clostridium medium (RCM) and incubated at anaerobic condition for 24 hrs. 24 hr to 48 hrs culture at Optical Density at 625 nm was determined 0.632 (1:2 dilution) 4.0 Macfarland standards.

Procedure 30 ml of sterilized RCM was poured into the pre-sterile Petri plates inside the chamber and allowed to solidify. The culture was inoculated (0.2 ml/plate) and spread evenly. After 30 minutes, antibacterial sterile discs (6 mm) were dispensed. Samples in varying concentrations (0.4-5% w/v) were prepared using dimethylsulphoxide (DMSO) as the solvent. 10 µl of the prepared sample and controls were dispensed onto the discs. The plates were incubated inside the anaerobic chamber at 37° C. for 24 to 48 hours duration.

Results and Discussion (Table B)

TABLE B

| Sample: Resveratrol Batch: C81173 Concentration of sample % (w/v) | Zone of inhibition (mm) | Sample: 3-Hydroxy Pterostilbene Batch: P80096 Concentration of sample % (w/v) | Zone of inhibition (mm) |
|---|---|---|---|
| 5.0 | 13.0 | 5.0 | 18.0 |
| 2.5 | 13.0 | 2.5 | 17.0 |
| 1.25 | 12.0 | 1.25 | 15.0 |
| 0.625 | 10.0 | 0.625 | 13.0 |
| 0.31 | No zone | 0.31 | 10.0 |
| 0.156 | No zone | 0.156 | No zone |
| 0.078 | No zone | 0.078 | No zone |
| DMSO | No zone | DMSO | No zone |

Clindac A.RTM. (Galderma India Pvt. Ltd., Mumbai) Anti-Acne Gel was used as Reference Standard (Table C)

TABLE C

| Clindamycin phosphate USP (Anti acne cream) SL. No. | Concentration (% w/v) | Zone of inhibition (mm) |
|---|---|---|
| 01 | 1 | 8.0 |
| 02 | 0.1 | No-zone |
| 03 | 0.05 | No-zone |
| Sterile water | As such | No-zone |

Sample preparation: sterilized DM water

Discussion and Inference

From the studies 3-Hydroxy pterostilbene at 3.12 mg/ml (0.312% w/v) concentration produced a zone of inhibition of 10 mm while a higher concentration of resveratrol 6.25 mg/ml (0.625% w/v) was required to produce a similar effect. Reference standard Clindac®, produced a 8 mm zone of inhibition at a concentration of 10 mg/ml (1.0% w/v).

Inhibitory Concentration ($IC_{50}$ and $IC_{100}$) Evaluation Studies

Method: Broth dilution method to evaluate the inhibitory concentration (IC).

Materials
1. *Propionibacterium acnes* ATCC: 11827
2. Physiological saline or Buffered peptone water (BPW).
3. Reinforced clostridium medium (RCM) Hi-media
4. Actinomyces broth (AC broth) Hi-media
5. Anaerobic chamber.
6. Gassing manifold Nitrogen, mixed gases.
7. Spectrophotometer (600 nm to 625 nm)
8. Sterile tubes
9. Micro Pipette
10. Sterile micro tips.
11. (DMS0) dimethylsulphoxide The strain *Propionibacterium acnes* (ATCC 11827) was obtained from ATCC. The inhibitory concentration (IC) of the given sample was determined by broth dilution method according to NCCLS guidelines. The $IC_{50}$ was defined as that concentration of compound that reduced bacterial growth by 50% as determined spectrophotometrically. $IC_{100}$ was defined as the lowest concentration of compound that inhibited bacterial growth by 100%. Resveratrol and 3-Hydroxypsterostilbene are water insoluble. Therefore samples were dissolved in DMSO and then added to Actinomyces broth to a final concentration of 0-500 mg/L. Twenty-four hour cultures of *P. acnes* were adjusted to $1\times10^8$ cfu/ml using McFarland standards and inoculated to Actinomycetes broth containing a specific concentration of compound. Controls containing just DMSO were also included in the test. Cultures were incubated anaerobically at 37° C. and read spectrophotometrically at 600 nm both at 24 h and 48 h incubation periods. $IC_{50}$ and $IC_{100}$ values were calculated from these observations.

TABLE D

| | | | | Results | | |
|---|---|---|---|---|---|---|
| Sample | Conc. (mg/L) | Dilution | OD at 600 nm 24 h | (IC) Inhibitory concentration | OD at 600 nm 48 h | (IC) Inhibitory concentration |
| AC broth | NA | As such | 0.131 | NA | 0.126 | NA |
| AC broth + culture | NA | 1:2 | 0.942 | NA | 0.820 | NA |
| 3-Hydroxy pterostilbene | 16.6 | 1:2 | 0.526 | IC 45 | 0.443 | IC 45 |
| | 41.6 | 1:2 | 0.352 | IC 62 | 0.338 | IC 62 |
| | 83.3 | As such | 0.047 | IC 98 | 0.073 | IC 98 |
| | 166 | As such | — | IC 100 | — | IC 100 |
| | 332 | As such | — | IC 100 | — | IC 100 |
| Resveratrol | 16.6 | 1:2 | 1.027 | No inhibition | 0.884 | No inhibition |
| | 41.6 | 1:2 | 0.777 | IC 17 | 0.593 | IC 27 |
| | 83.3 | 1:2 | 0.423 | IC 55 | 0.573 | IC 30 |
| | 166 | 1:2 | 0.232 | IC 75 | 0.268 | IC 68 |
| | 332 | As such | 0.00 | IC 100 | 0.11 | IC 85 |
| | 498 | As such | — | IC 100 | 0.00 | IC 100 |

NA: Not applicable

Discussion and Inference (Table E)

TABLE E

| SAMPLE | STRAIN | IC50 (mg/L) 24 h | IC100 (mg/L) 24 h | IC50 (mg/L) 48 h | IC100 (mg/L) 48 h |
|---|---|---|---|---|---|
| 3-Hydroxy pterostilbene P80096 | *P. acnes* ATCC 11827 | 33.5 | 83.3 | 35.8 | 83.0 |
| Resveratrol C81173 | *P. acnes* ATCC 11827 | 83.0 | 332.0 | 120 | 498 |
| DMSO | *P. acnes* ATCC 11827 | No inhibition | No inhibition | No inhibition | No inhibition |

Conclusion

From the inhibitory concentration studies, both Resveratrol and 3-HydroxypteroStilbene were capable of inhibiting *P. acnes* growth. 3-Hydroxypterо-stilbene was found to be more effective against *P. acnes*. 3-hydroxypterostilbene showed 100% inhibition of *Propionilyacierium acnes* at concentrations of 83.3 mg/ml and 83 mg/ml following 24 hours and 48 hours of incubation respectively. While resveratrol showed 100% inhibition of *Propionibacterium acnes* at concentrations of 332 mg/ml and 498 mg/ml following 24 hours and 48 hours of incubation respectively.

EXAMPLE 4

Pharmacokinetic Studies

Figure 2A:
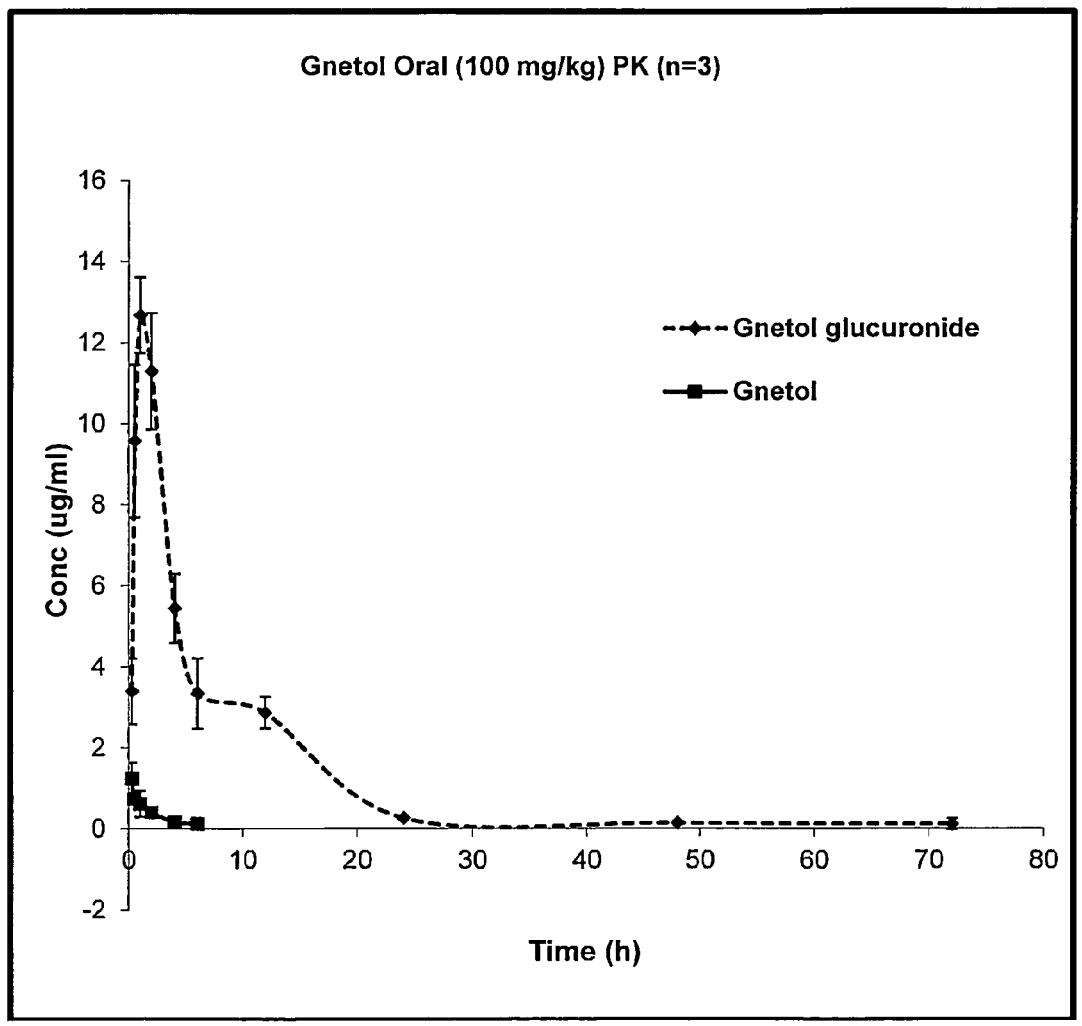
FIGS. 2A and 2B show the graphical representations of 2,3',5',6-tetrahydroxy-trans-stilbene (gnetol) pharmacokinetics in the serum upon oral administration in animals.
Figure 2B:
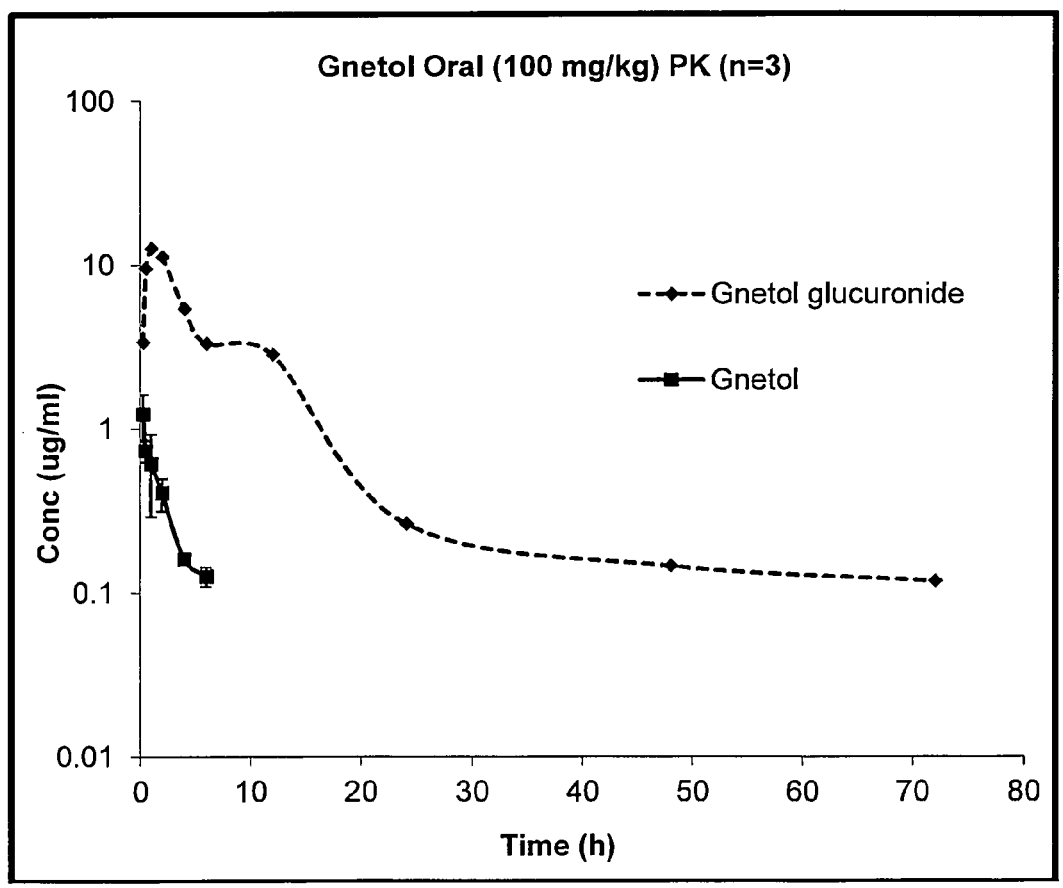
Figure 3A:
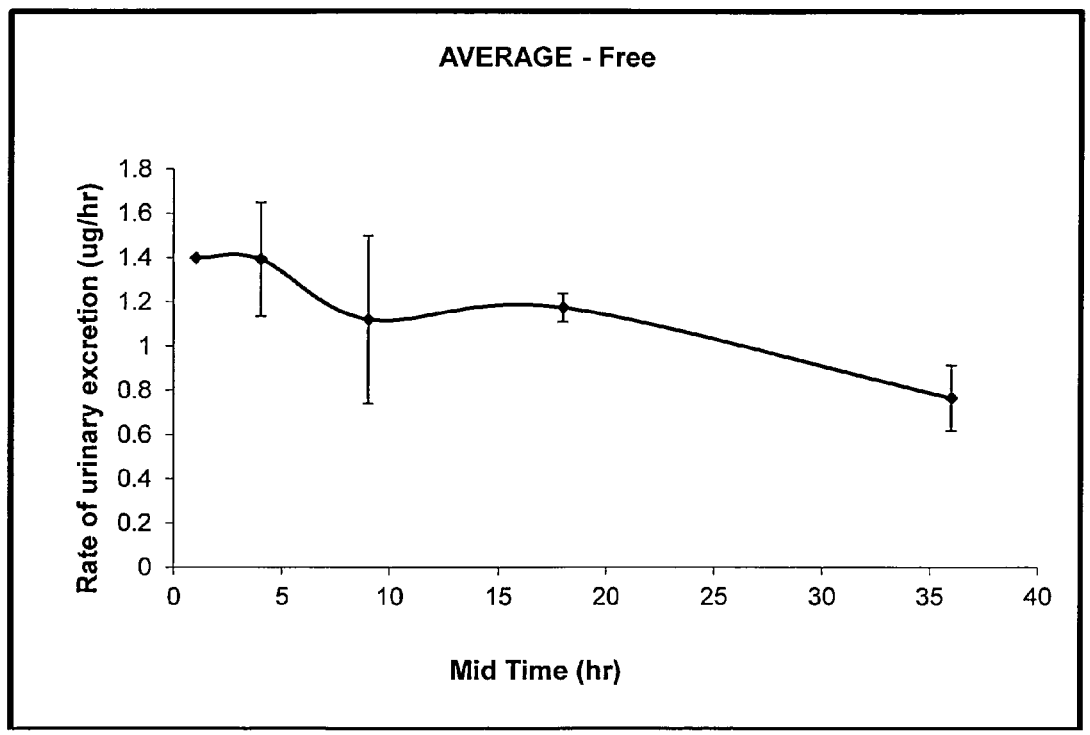
FIGS. 3A, 3B and 3C shows the graphical representations of 2,3',5',6-tetrahydroxy-trans-stilbene (gnetol) pharmacokinetics in the urine upon oral administration in animals.
Figure 3B:
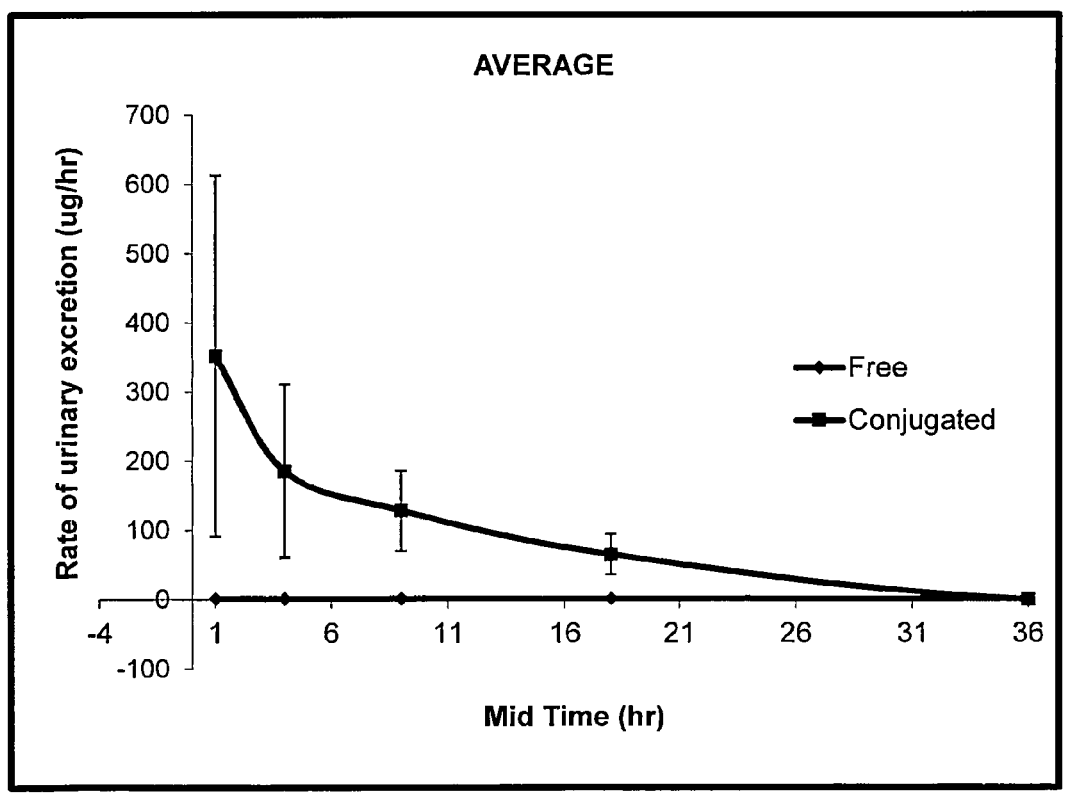
Figure 3C:
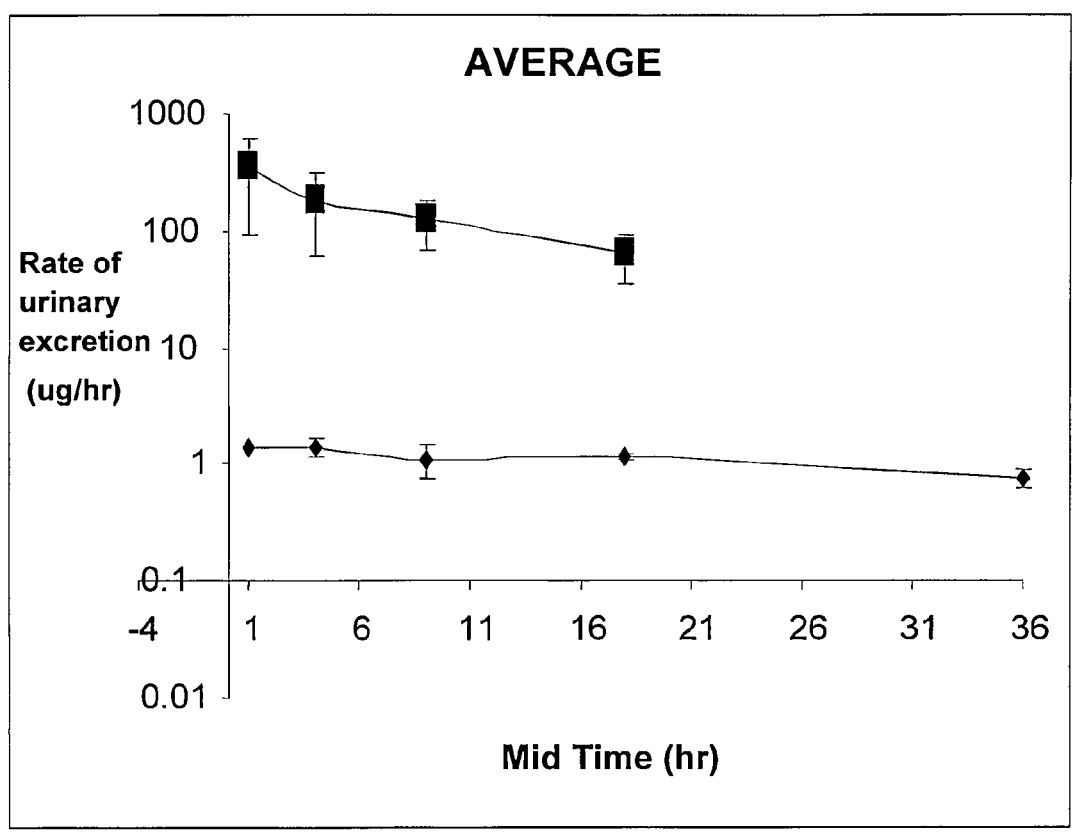

FIGS. 2A and 2B reveal that upon oral administration in rats of 100 mg/kg body weight, it is evident that 2,3',5,6-tetrahydroxy-trans-stilbene (genetol) in its free form and as a glucoromide is orally bioavailable. The compound in its free and conjugated form is freely absorbed into systemic circulation with the glucoronide detected up to 72 hours. FIGS. 3A, 3B and 3C reveal that 2,3',5',6-tetrahydroxy-trans-stlibene (gnotol) is excreted predominantly as glucoronides in the urine, with glucoronides exhibiting a better rate of excretion.

Figure 4:
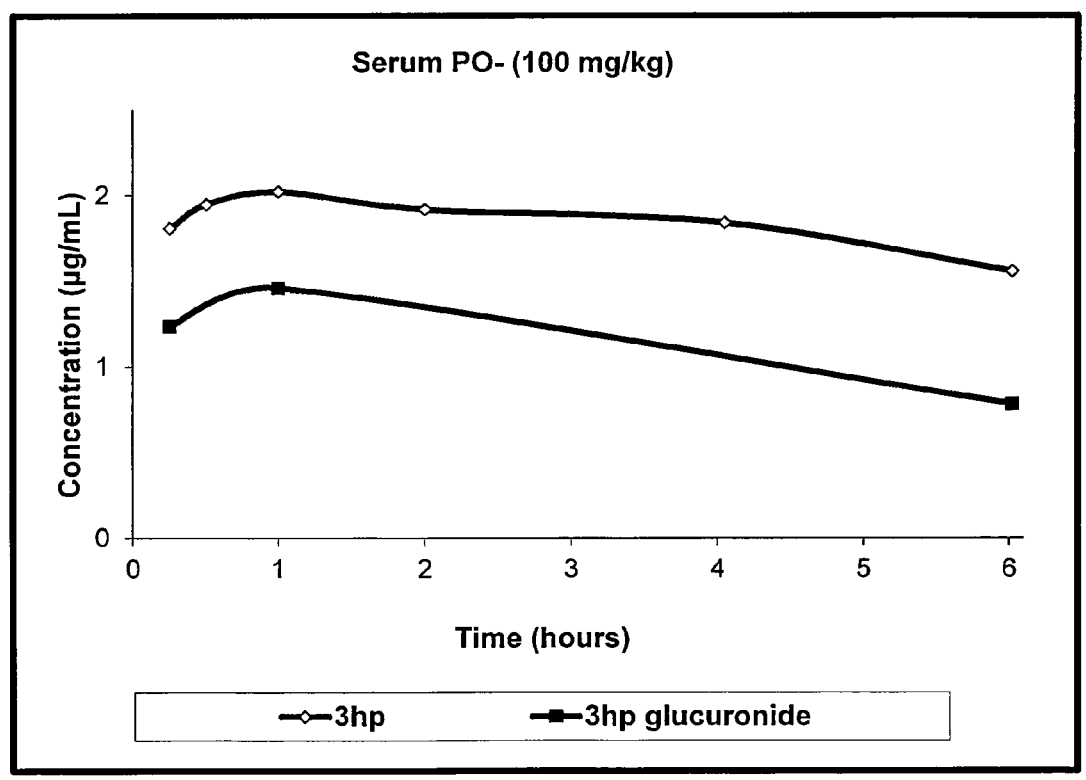
FIG. 4 shows the graphical representations of 3,5-dimethoxy-3,4'-dihydroxystilbene pharmacokinetics in the serum upon oral administration in animals.
Figure 5A:
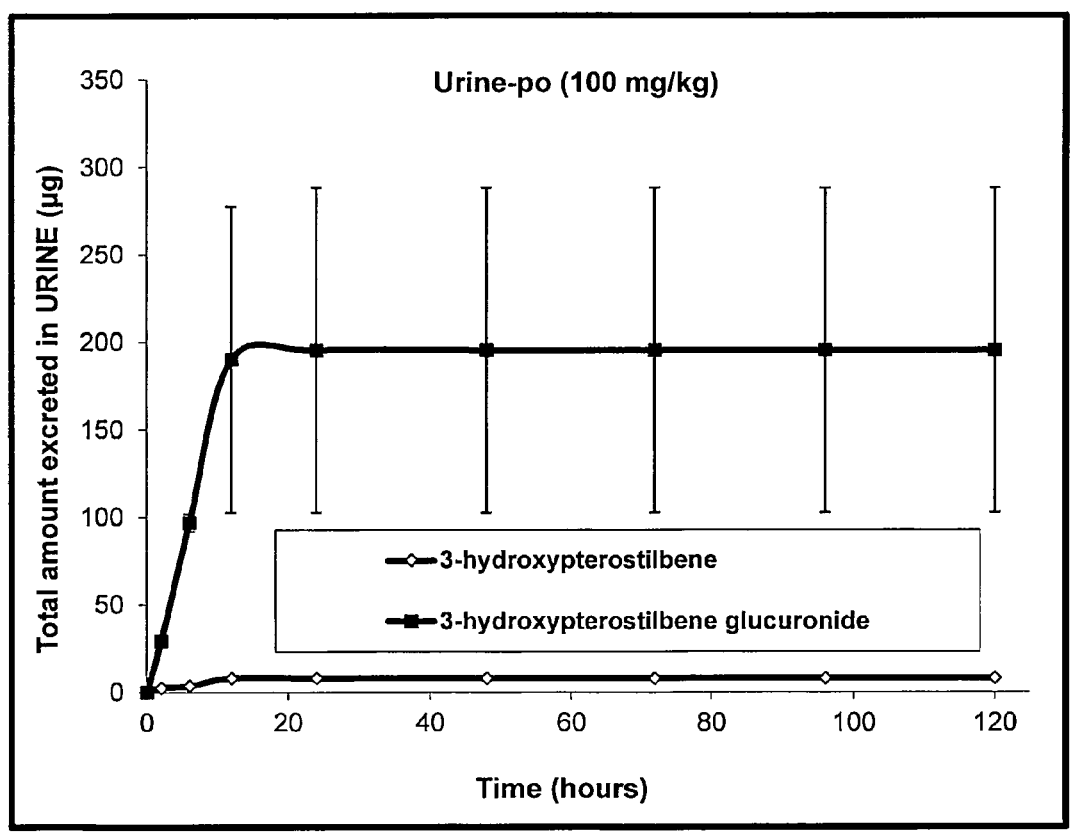
FIGS. 5A and 5B shows the graphical representations of 3,5-dimethoxy-3,4'-dihydroxystilbene pharmacokinetics in the urine upon oral administration in animals.
Figure 5B:
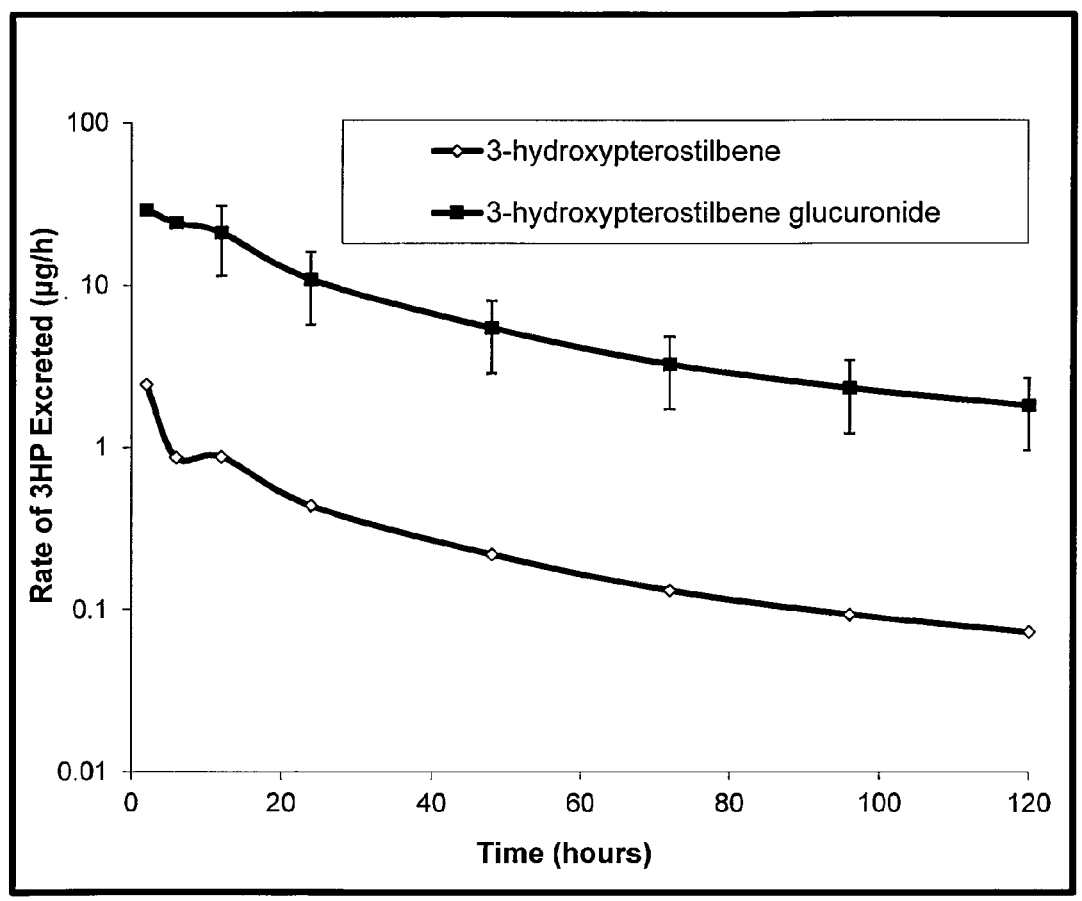

Upon oral administration in rats of 100 mg/kg body weight, it is evident that 3,5-dimethoxy-3,4'-dihydroxystilbene (3-hydroxypterostilbene) in its free form and as a glucoronide is orally bioavailable. (FIG. 4). The compound in its free and conjugated form appears in systemic circulation within 15 minutes of administration. 3,5-dimethoxy-3,4'-dihydroxystilbene (3-hydroxypterostilbene) is excreted predominantly as glucoronides in the urine, with glucoronides exhibiting a better rate of excretion (FIGS. 5A and 5B).

References

1. John J. Docherty, Heather A. McEwen, Thomas J. Sweet, Erin Bailey and Tristan D. Booth: "Resveratrol inhibition of *Propionibacterium acnes*"; Journal of antimicrobial chemotherapy (2007) 59, 1182-1184. Advance Access publication 21 Apr. 2007;

2. National committee for clinical laboratory standards-Methods for Antimicrobial susceptibility testing of Anaerobic Bacteria-fifth edition: Approved standards M11-A6.NCCLS, Wayne, Pa., USA, 2000.

EXAMPLE 5

Formulations

Cosmeceutical formulations comprising 3,5-dimethoxy-3,4'-dihydroxystilbene (3-hydroxypterostilbene)

Cosmeceutical Formulation I

| S. No. | Formula | Content % w/w |
|---|---|---|
| 1 | 3,5-dimethoxy-3,4'-dihydroxystilbene | 0.25-5 |
| 2 | Tetra sodium EDTA | 0.02 |
| 3 | Imidurea | 0.15 |
| 4 | Sodium Methyl paraben | 0.20 |
| 5 | Sodium Propyl paraben | 0.02 |
| 6 | Propylene glycol | 2.00 |
| 7 | Carbopol U-10 | 0.20 |
| 8 | Pemulene TR-1 | 0.15 |
| 9 | GMS SE | 1.00 |
| 10 | Arlatone 2121 | 1.00 |
| 11 | Arlacel 165 | 1.00 |
| 12 | Elsoft | 2.00 |
| 13 | Elcast H | 2.00 |
| 14 | Sodium Hydroxide (20% NaOH solution) | 0.10 |
| 15 | DC 3031 Fluid | 0.50 |
| 16 | Demineralised water | 84.66-89.41 |
| | | 100.00 |

Cosmeceutical Formulation II

| S. No. | Formula | Content % w/w |
|---|---|---|
| 1 | 3,5-dimethoxy-3,4'-dihydroxystilbene | 0.25-5 |
| 2 | Tetra sodium EDTA | 0.02 |
| 3 | Imidurea | 0.15 |
| 4 | Sodium Methyl paraben | 0.20 |
| 5 | Sodium Propyl paraben | 0.02 |
| 6 | Propylene glycol | 2.00 |
| 7 | Carbopol U-10 | 0.30 |
| 8 | Pemulene TR-1 | 0.20 |
| 9 | GMS SE | 1.00 |
| 10 | Arlatone 2121 | 1.00 |
| 11 | Arlacel 165 | 1.00 |
| 12 | Fluilan (Liquid lanolin) | 2.00 |
| 13 | CCTG | 2.00 |
| 14 | Kokum butter | 0.50 |
| 15 | Sodium Hydroxide (20% NaOH solution) | 0.10 |
| 16 | DC 3031 Fluid | 0.50 |
| 17 | Demineralised water | 84.01-88.76 |
| | | 100.00 |

Cosmeceutical Formulation III

| S. No. | Formula | Content % w/w |
|---|---|---|
| 1 | 3,5-dimethoxy-3,4'-dihydroxystilbene | 0.25-5 |
| 2 | Carbopol U-10 | 0.20 |
| 3 | Pemulene TR-1 | 0.15 |
| 4 | Glycerine | 2.00 |
| 5 | Arlatone 2121 | 1.00 |
| 6 | GMS SE | 2.00 |
| 7 | Crill 4 | 2.00 |
| 8 | Jojoba oil | 2.00 |
| 9 | Kokum butter | 0.50 |
| 10 | Triethanolamine | 1.00 |
| 11 | Neolon PE | 0.50 |
| 12 | Demineralised water | 84.70-87.45 |
| | | 100.00 |

Cosmeceutical Formulation IV (Lotion)

| S. No. | Formula | Content % w/w |
|---|---|---|
| 1 | 3,5-dimethoxy-3,4'-dihydroxystilbene | 0.25-5 |
| 2 | Tetra sodium EDTA | 0.05 |
| 3 | Imidurea | 0.50 |
| 4 | Methyl paraben | 0.25 |
| 5 | Propyl paraben | 0.10 |
| 6 | Propylene glycol | 3.00 |
| 7 | Glycerine | 3.00 |
| 8 | GMS SE | 1.00 |
| 9 | CCTG | 1.00 |
| 10 | Iso Propyl Myristate | 2.00 |
| 11 | Light liquid Prarffin | 1.75 |
| 12 | Soft Paraffin | 1.00 |
| 13 | Polawax | 1.00 |
| 14 | DC 3031 Fluid | 0.30 |
| 15 | Salcare SC-91 | 0.60 |
| 16 | Demineralised water | 79.45-84.20 |
| | | 100.00 |

Nutraceutical/Pharmaceutical Formulations 3-hydroxypterostilbene Tablet

Label Claim: Each tablet contains: 3-hydroxypterostilbene=250 mg

Composition

| 1. | 3-hydroxypterostilbene = | 250 mg |
|---|---|---|
| 2. | Microcrystalline cellulose BP = | 190.0 mg |
| 3. | Maize Starch BP = | 40.0 mg |
| 4. | Magnesium Stearate BP = | 5.0 mg |
| 5. | Sodium Starch Glycolate BP = | 15.0 mg |

3-hydroxypterostilbene Capsules
Label Claim: Each Capsule contains 3-hydroxypterostilbene=250 mg
Composition

| 1. | 3-hydroxypterostilbene = | 250 mg |
|---|---|---|
| 2. | Microcrystalline cellulose BP = | 38.0 mg |
| 3. | Maize Starch BP = | 10.0 mg |
| 4. | Magnesium Stearate BP = | 2.0 mg |
| 5. | Hard Gelatin Capsules Size'1' | |

Gnetol Capsules
Label Claim: Each Capsule contains: Gnetol=250 mg
Composition

| 1. | Gnetol = | 250 mg |
|---|---|---|
| 2. | Microcrystalline cellulose BP = | 38.0 mg |
| 3. | Povidone BP = | 10.0 mg |
| 4. | Magnesium Stearate BP = | 2.0 mg |
| 5. | Hard Gelatin Capsules Size'1' | |

Gnetol Tablets
Label Claim: Each tablet contains Gnetol=250 mg
Composition

| 1. | Gnetol = | 250 mg |
|---|---|---|
| 2. | Microcrystalline cellulose BP = | 190.0 mg |
| 3. | Povidone BP = | 40.0 mg |
| 4. | Magnesium Stearate BP = | 5.0 mg |
| 5. | Sodium Starch Glycolate BP = | 15.0 mg |

3-hydroxypterostilbene and Gnetol Tablets
Label Claim: Each tablet contains 3-hydroxypterostilbene=100 mg AND Gnetol=100 mg
Composition

| 1. | 3-hydroxypterostilbene = | 100 mg |
|---|---|---|
| 2. | Gnetol = | 100 mg |
| 3. | Microcrystalline cellulose BP = | 240.0 mg |
| 4. | Maize Starch BP = | 40.0 mg |
| 5. | Magnesium Stearate BP = | 5.0 mg |
| 6. | Sodium Starch Glycolate BP = | 15.0 mg |

3-hydroxypterostilbene and Epicatechin Capsules
Label Claim: Each tablet contains 3-hydroxypterostilbene=250 mg and Epicatechin=25.0 mg
Composition

| 1. | 3-hydroxypterostilbene = | 250 mg |
|---|---|---|
| 2. | Epicatechin = | 25.0 mg |
| 3. | Microcrystalline cellulose BP = | 13.0 mg |
| 4. | Maize Starch BP = | 10.0 mg |
| 5. | Magnesium Stearate BP = | 2.0 mg |
| 6. | Hard Gelatin Capsules Size'1' | |

EXAMPLE 6

In-House Data for Miscellaneous Properties of 3,5-dimethoxy-3,4'-dihydroxystilbene (Table F)

TABLE F

| Test | Result |
|---|---|
| ANTI OBESITY POTENTIAL | |
| Adipogenesis inhibitory assay | $IC_{50}$ is 4.83 nM |
| SKIN LIGHTENING POTENTIAL | |
| Melanin inhibitory assay in B16F1 mouse melanoma cell line | $IC_{50}$ is 0.7 µg/ml |
| ANTI TYROSINASE ACTIVITY | $IC_{50}$ is 2 µg/ml |
| ANTIOXIDANT POTENTIAL | |
| Oxygen Radical Absorbance Capacity (ORAC) | 13334 ± 323 µmol TE/100 g |
| DPPH scavenging assay | $SC_{50}$ is 1.34 µg/ml |
| ANTI INFLAMMATORY POTENTIAL | |
| Anti collagenase assay | $IC_{50}$ is 90 µg/ml |
| Anti Elastase assay | $IC_{50}$ is 82 µg/ml |
| ANTI α-GLUCOSIDASE ACTIVITY | $IC_{50}$ is 203.7 µg/ml |

Safety Data:

3-hydroxypterostilbene is non mutagenic in the Bacterial reverse mutation assay (AMES), both in the presence and absence of metabolic activation, upto a workable concentration of 415 µg/ml.

Repeated dose 90 day Oral toxicity study for 3HPT in Sprague Dawley rats: The study was conducted to evaluate the possible health hazards likely to arise from repeated exposure to 3HPT over a relatively limited period of time. The study was conducted in six groups consisting of 120 rats with 60 males and 60 females. Group-I, I (R), II, III, IV and IV (R) served as Control, Control Recovery, Low dose (20 mg/kg Bwt), Mid dose (80 mg/kg Bwt), High dose (200 mg/kg Bwt) and High dose Recovery (200 mg/kg Bwt) groups respectively. The test item or vehicle was administered through oral route by gavage to animals daily for 90 days. The animals of Control group and Control recovery group were administered with Corn oil. The vehicle and test item administration to Control Recovery and High dose Recovery group animals respectively was stopped after 90 days of administration and observed for another 28 days to evaluate the effects during recovery period. The animals were observed for health status, clinical signs of toxicity and mortality, weekly detailed veterinary examination and subjected to neurological examination. Body weights and food consumptions were recorded at weekly intervals. On completion of 90 days for treatment groups or 118 days for recovery groups respectively, the blood samples were collected from all the animals and subjected to haematological and clinical chemistry evaluation. At termination the animals were humanely sacrificed and subjected to necropsy examination. Histopathological examination was conducted on the specified list of tissues from the control and the high dosage level group. Significant reduction in body weights and body weight gain observed in both the sexes at 200 mg/kg Bwt was considered non adverse. Food consumption was comparable across the groups. The haematological and clinical chemistry data did not show any statistical significance at all the doses tested. Necropsy and histopathology examination of tissues and organs did not reveal any pathological changes. From the results of the study, the No-Observed-Adverse-Effect-Level (NOAEL) of 3-HY- DROXYPTEROSTILBENE in Sprague Dawley rats, following oral route administration for 90 days was found to be 200 mg/kg Bwt.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of adipogenesis inhibition, said method comprising step of bringing into contact subject adipocytes and an effective concentration of 3,5-dimethoxy-3, 4'-dihydroxystilbene represented by STR#I

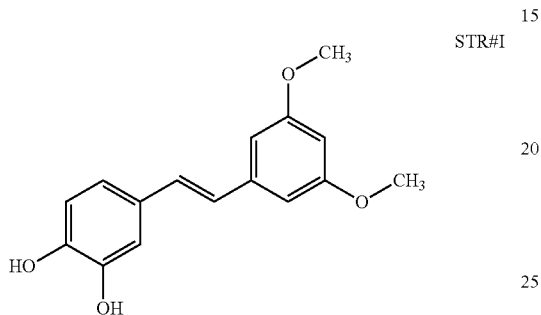

STR#I

* * * * *